United States Patent [19]

Hohmann et al.

[11] Patent Number: 4,891,041

[45] Date of Patent: Jan. 2, 1990

[54] DEVICE FOR SEPARATING SOLIDS FROM LIQUIDS IN A DENTAL APPARATUS

[75] Inventors: Eugen Hohmann, Bensheim; Wolfgang Behringer, Bensheim-Wilmshausen; Manfred Preuss, Lautertal, all of Fed. Rep. of Germany

[73] Assignee: Siemens Aktiengesellschaft, Berlin and Munich, Fed. Rep. of Germany

[21] Appl. No.: 192,938

[22] Filed: May 12, 1988

[30] Foreign Application Priority Data

May 13, 1987 [DE] Fed. Rep. of Germany ....... 3716008
Jul. 27, 1987 [DE] Fed. Rep. of Germany ....... 3724841

[51] Int. Cl.⁴ .............................................. B04B 7/02
[52] U.S. Cl. ........................................ 494/62; 494/80; 494/84
[58] Field of Search .................. 494/27, 29, 30, 60, 494/61, 62, 63, 79, 80, 83, 84; 210/781, 782; 422/72

[56] References Cited

U.S. PATENT DOCUMENTS

| | | | |
|---|---|---|---|
| 1,828,096 | 10/1931 | Bryson | 494/60 X |
| 1,924,676 | 4/1934 | Lindberg | 494/80 X |
| 1,981,924 | 11/1934 | Reese et al. | |
| 2,140,388 | 12/1938 | Lucas | 494/80 |
| 2,213,107 | 8/1940 | Mc Bain | 494/80 |
| 2,353,983 | 7/1944 | Banning | 494/80 X |
| 4,140,270 | 2/1979 | Dowd et al. | 494/79 X |
| 4,356,959 | 11/1982 | Rosander | 494/60 |
| 4,663,035 | 5/1987 | Rosander | |

FOREIGN PATENT DOCUMENTS

| | | |
|---|---|---|
| 0023036 | 10/1983 | European Pat. Off. . |
| 0224232 | 6/1987 | European Pat. Off. . |
| 3521929 | 1/1986 | Fed. Rep. of Germany . |
| 1380872 | 10/1964 | France . |
| 238684 | 11/1945 | Switzerland . |
| 1507742 | 4/1978 | United Kingdom . |
| WO 86/03669 | 7/1986 | World Int. Prop. O. . |

Primary Examiner—Robert W. Jenkins
Attorney, Agent, or Firm—Hill, Van Santen, Steadman & Simpson

[57] ABSTRACT

A separating device which utilizes a centrifuge which is driven by a motor for processing liquids enriched with solids by forcing the solids out of the liquid against a peripheral centrifuge wall as a consequence of centrifugal force characterized that a collecting vessel is the centrifuged container. The collecting vessel or centrifuge chamber has a plurality of axially spaced partitions with concentrically arranged openings to form axially spaced chambers which will collect the solids separated from the liquid as the liquid is discharged from the device. In one embodiment, the collecting vessel and centrifuge chamber are a single molded member. In another embodiment, there are two parts, with one being a container-like part receiving an insert having the parititons.

15 Claims, 3 Drawing Sheets

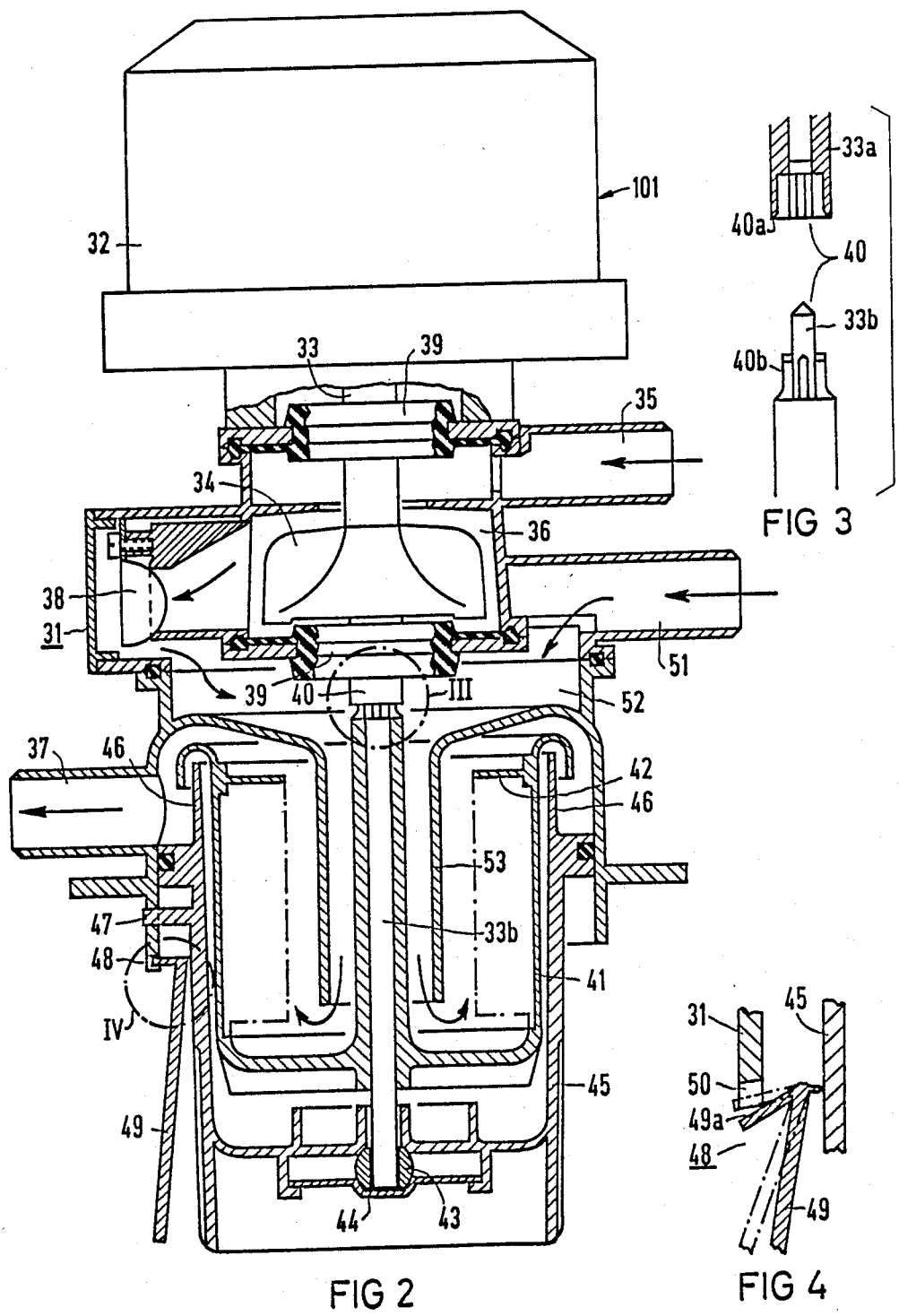

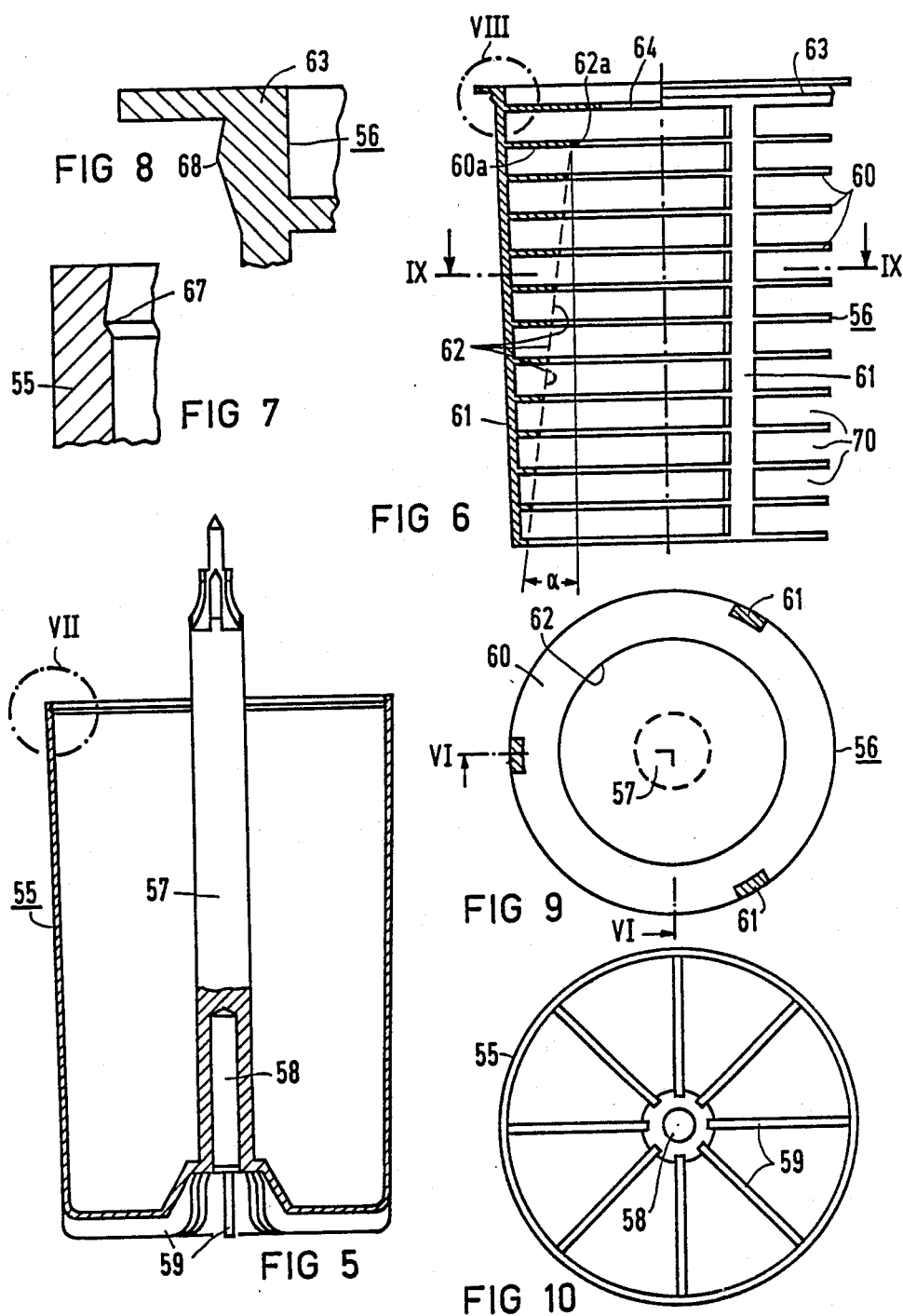

DEVICE FOR SEPARATING SOLIDS FROM LIQUIDS IN A DENTAL APPARATUS

BACKGROUND OF THE INVENTION

The present invention is directed to a device for separating solids, particularly amalgam, from liquids in dental apparatus. The device includes a centrifuge which has a container that is driven by a motor and which centrifuge has an admission channel through which a liquid enriched with solids is introduced to the centrifuge so that the solids may be forced to a peripheral centrifuge wall of the container as a consequence of centrifugal forces and the liquid overflows the container and out through an outlet channel and which centrifuge has a collecting vessel in which the solids are collected and kept.

An apparatus for separating air and solid particles from liquid is disclosed in U.S. Pat. No. 4,663,035, whose disclosure is incorporated by reference and which claims priority from the same Swedish application as German AS 35 21 929.

A disadvantage in this known device is that, due to adhesion, particles of solids will adhere to an inside surface of the centrifuge. This adhesion is especially established given extremely small particles which are less than 0.5 mm and the adhesion continues to exist even when the centrifuge is brought to a standstill. A fast deceleration is provided in order to nonetheless transport these particles into a collecting vessel. However, practical tests have shown that the adhesion force predominates over the deceleration forces so that a great quantity of the small particles continue to remain in the centrifuge. Another problem with this known apparatus is that it is rather involved in structure.

SUMMARY OF THE INVENTION

The present invention is directed to providing an improvement in a device for separating solids from a liquid, particularly used in a dental apparatus. These objects are achieved in an improvement in a device for separating the solids, which has a centrifuge with a rotating container which is driven by a motor, said centrifuge having an admission channel through which a liquid enriched with solids is introduced to the interior of the container so that the solids may be centrifuged against a peripheral centrifugal wall as a consequence of centrifugal forces, the centrifuge also includes an outlet channel through which the liquid that overflows from the container can be conducted out of the device and has a collecting vessel in which the centrifugal solids are collected and kept. The improvements are that the collecting vessel is a component part of the rotating container of the centrifuge with the wall of the vessel forming the centrifugal wall, said collecting vessel comprising a plurality of partitions extending transversely relative to a dynamically balanced axis of the shaft of the motor to form a plurality of chambers positioned along the axis of the shaft, said chambers being connected both to one another, as well as to the outlet channel by an opening in the center of each partition so that the fluid can move parallel to the axis and coupling means for connecting the collecting vessel to the drive shaft with torsionally rigid and axially detachable connections.

According to the invention, the collecting vessel for the particles is a component part of the rotating system and, thus, forms a compact unit together with the rotor shaft. However, it is constructed so that it can be easily separated or detached therefrom. The collecting vessel contains a plurality of partitions which are arranged perpendicularly relative to the rotary axis and which form chambers arranged one above the other. The ratio of the diameter of the chambers to the height of these chambers amounts to about 5:1. It is especially advantageous when the tubular nozzle for the liquid is arranged to be concentric relative to the drive shaft and that this nozzle extends through the vessel to a discharge point adjacent the lower third of the collecting vessel so that the partitions comprise correspondingly large concentric openings that also guarantee the passage of the liquid. The collecting vessel is expediently fashioned as a throw-away or disposable container and is composed of environmentally safe material, for example of polypropylene or polysulphone.

In accordance with the advantageous development of the invention, the drive motor for the centrifuge is likewise provided as a drive motor for a pump pressing or drawing the liquid into the collecting vessel. This pump is advantageously arranged as an integral part in an upper part of the housing of the centrifuge. The overall drive system is suspended in a low vibration fashion. To this end, the drive shaft is advantageously transversely divided and the shaft section for placing the collecting vessel into rotation is elastically seated so that one bearing faces toward the collecting vessel is accepted by a cup-shaped lower part of the housing that surrounds the collecting vessel.

The degree to which the collecting vessel is filled is advantageously monitored by measuring the start-up time of the motor to which end corresponding sensor elements measure the start-up time are present and these supply a signal for an optical and/or acoustical display when a defined or predetermined start-up time allocated to the maximum loading of the container has been exceeded.

Other advantages and features of the invention will be readily apparent from the following description of the preferred embodiments, drawings and claim.

BRIEF DESCRIPTION OF THE DRAWINGS

FIG. 2 is a longitudinal cross sectional view with portions in elevation for purposes of illustration of a second embodiment of the invention;

FIG. 3 is a partial enlarged cross sectional view with portions in elevation of the portion contained in circle III of FIG. 2 in a disassembled condition;

FIG. 4 is an enlarged cross sectional view of the portion contained in circle IV of FIG. 2;

FIG. 5 is a partial cross sectional view with portions in elevation for purposes of illustration of an outer part of a third embodiment of the invention;

FIG. 6 is a view taken along the lines VI—VI of FIG. 9 of an insert of the third embodiment;

FIG. 7 is an enlarged partial cross sectional view taken in the area of circle VII of FIG. 5;

FIG. 8 is an enlarged view taken in circle VIII of FIG. 6;

FIG. 9 is a cross sectional view taken along the lines IX—IX of FIG. 6; and

FIG. 10 is a bottom end view of the container of FIG. 5.

DESCRIPTION OF THE PREFERRED EMBODIMENTS

Figure 1:
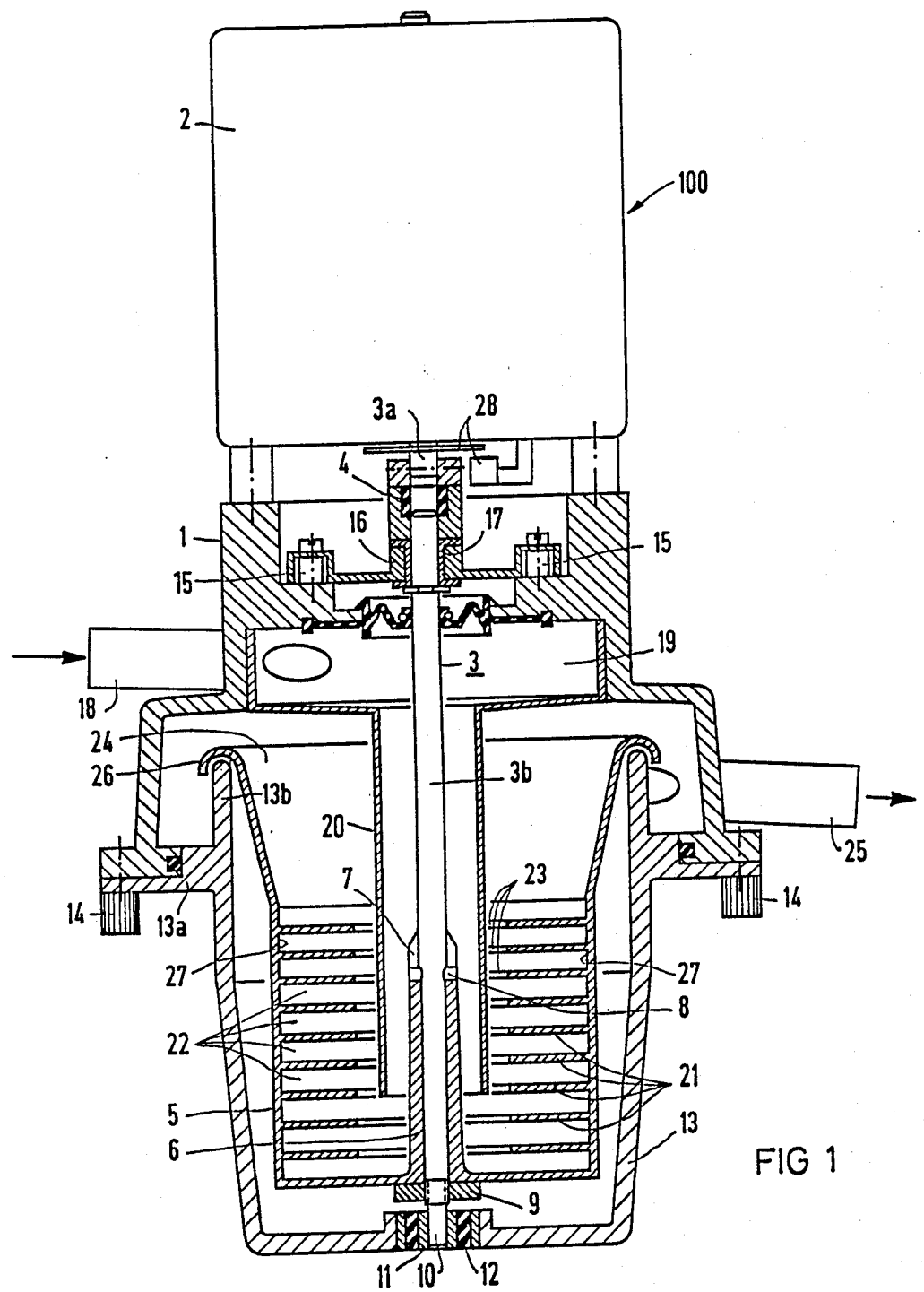
FIG. 1 is a longitudinal cross section with portions in elevations for purposes of illustration of a first embodiment of the present invention.

The principles of the present invention are particularly useful when incorporated in a separating device generally indicated at 100 in FIG. 1. The device 100 includes an upper housing part 1, which has a pot-shape, and a lower housing part 13. A drive motor 2, which is an electric motor, has a vertical drive shaft 3 and is secured to an upper surface of the pot-shaped upper housing part 1. The drive shaft 3 is transversely divided so that it has two shaft sections or portions 3a and 3b, which are formed by transverse division and are connected to one another by a coupling 4.

A dynamically balanced collecting vessel 5, which serves as a container for a centrifuge, is arranged and torsionally connected but axially detachable from a lower shaft section 3b. The collecting vessel or container 5 has a central hub 6 that allows the container to be axially slipped onto the lower shaft section 3b. In the upper part, the hub 6 is provided with a slot 7 in which a dog pin 8 that extends transversely relatively to the longitudinal axis of symmetry is engaged to insure transfer of the torsion from the shaft 3b to the hub 6. After slipping the collecting vessel 5 axially onto the shaft 3, a locking ring 9 can be secured to the base of the shaft, such as by being threaded thereto.

A free end 10 of the shaft section 3b is received in a bearing 11 that has an elastic means 12, and this bearing 11 with the elastic means 12 is secured or mounted in a base of the lower housing part 13, which surrounds the collecting vessel 5. As illustrated, the lower housing part 13 has an annular radially extending flange 13a and an annular upwardly extending lip 13b. The lower housing part 13 is connected to the upper housing part 1 by threaded fasteners which engage the annular flange 13a as the lip portion 13b extends into a cavity of the housing part 1.

The upper end of the shaft 3b is, likewise, mounted in a low-vibration fashion in the region of the coupling 4 with the assistance of an elastic means 15. These are supported, first, against an upper housing part 1 and, secondly, at a carrying part 16 for the additional shaft bearing 17. The upper housing part 1 has an admission or entrance channel 18 that is connected to that part of the suction means at a suction side in a known way and via which liquid enriched with solid particles, such as an amalgam, gold particles, etc., can enter into an annular distribution space 19 in the housing part 1. The annular distribution space 19 has a pipe-shaped nozzle 20, which extends concentrically downward around the shaft 3b to approximately a base or floor of the collecting vessel 5. Preferably, the nozzle 20 extends at least to the lower third of the vessel 5.

The collecting vessel 5 has a plurality of transversely extending partitions 21 which are spaced along the axis of the device and form a multitude of chambers 22, which are connected both to one another by central openings 23 which are arranged concentrically relative to the hub 6 and relative to the nozzle 20. In addition, these chambers 22 are connected to the container opening 24 at the upper end of the container. The openings 23 are larger than the outside diameter of the nozzle 20 and are dimensioned so that a liquid introduced into the container via the admission channel 18 and the nozzle 20 can flow into the outlet channel 25 via the container opening 24 without backing up. So that the liquid cannot penetrate into the lower housing part 13, the top of the container 5 is provided with an edge or annular lip 26, which overlaps the upper annular edge 13b of the housing part 13.

The partitions 21 and the chambers 22 that are formed by the partitions serve the purpose of intercepting the entrained solid particles in a distributed fashion as they are pressed against the peripheral or outer wall 27 of the container 5 during the rotation of the container as a consequence of centrifugal forces. As tests have shown, a depositing of the solid or amalgam particles that are partly relatively specifically heavy can be achieved in a low-balance fashion in this way. During the course of employment, the chamber uniformly fills from bottom to top. Dependent on the container size, at least three such chambers are necessary, although, preferably, 10-12 chambers are provided in a container having a volume of 700 ml. The ratio between the diameter of the partitions to the height of the chambers (space between adjacent partitions) amounts to at least 5:1.

The liquid containing the solids enters through the nozzle 20 and is introduced practically in the proximity of the container floor as a consequence of the relatively deep immersion or extension of the nozzle into the container 5. Upon rotation of the container in a speed range of 2,500-3,000 rpm, the solid particles are uniformly distributed onto the chambers 22 and are centrifuged against the peripheral wall 27 of the container. During this, the liquid will be pressed up over the openings 23 and the container opening 24 into the outlet channel 25. As soon as a defined filling degree of the solid particles is obtained, an optical and/or acoustical signal will be given as an indication to change the container.

A system or means for sensing, when to change the container, utilizes a start-up time of the motor as an indicating measurement and, thus, monitors the time required to obtain the desired speed of the device. To this end, monitoring can be achieved, for example, by a light barrier arrangement 28 which is attached with portions on the upper shaft section 3a and a portion on a fixed housing part adjacent thereto. The start-up time of the motor until the nominal speed is reached is capable of being measured with this light barrier arrangement and this length of time will be ultimately dependent on the mass in the container and the moment of inertia of the container with the length of time increasing as the amount of filling increases. When a predetermined start-up time assigned to a predetermined filling capacity of the container has been exceeded, then the optical and/or acoustical signal can be actuated and, under given conditions, the motor can also be shut off.

An embodiment of the separator device is generally indicated at 101 in FIG. 2. In this embodiment, the device 101 includes a drive motor 32, which is secured to an upper surface of a housing part 31. In contrast to the embodiment of FIG. 1, the drive motor drives not only the centrifuge, but also a pump 34, which is positioned on a motor shaft 33. With the pump 34, the liquid suctioned out of a patient's mouth by a suction system and separated from air in a separating device, such as disclosed in European Pat. No. 00 23 036, is conducted by an admission channel 35 into a pump housing 36 and is then conducted with pressure into the centrifuge and is, subsequently, conducted via the outlet channel 37 into the discharge. A check valve 38 is situated at an outlet of the pump housing 36. The check valve is a hemispherical plastic part that is movably secured in a hinge-like fashion in the pump housing. Seals 39 are provided for sealing the motor shaft 33 in the pump housing 36.

The motor shaft 33 is transversely divided in the region of the circle III and contains a plug-in coupling 40, which is shown in a disassembled condition in FIG. 3. The plug-in coupling 40 is formed of polygonal profile parts 40a, which is a socket that mates with a part 40b to enable transmission of torque between the parts 33a and 33b, and also enables an uncoupling of these two shaft parts. The lower shaft section or part 33b is a component part of a collecting vessel 41 that is constructed in a fashion similar to the vessel 5 in FIG. 1 and, likewise, comprises a plurality of partitions 42 proceeding transversely relative to the axis of symmetry, although only one partition is illustrated in the drawing. Since, as already mentioned in the case of the first embodiment, the collecting vessel is advantageously composed of plastic and is expediently fashioned as a throw-away or disposable article, it is advantageous to fashion the lower shaft 33b and one coupling part 40b of the coupling 40 as a molded part together with the collecting vessel 41.

The lower end of the shaft 33b is seated in a bearing 43 which has a spherical outer surface and is held in a lower housing part 45 by a tensing or spring member 44. The lower housing part 45 is removable from the upper housing part so that the collecting vessel 41, together with its shaft section or part 33b can be easily removed and reintroduced therein. The housing wall 46 of the lower housing part 45 advantageously forms part of an outlet channel 37, and this housing part can be secured to the upper housing part with the bayonet closure 47. A latch means 48, which is shown in greater detail in FIG. 4, provides a twist-proof holding of the lower part 45 of the housing in the locked position of the bayonet closure. The latching is composed of a rocker arm 49 arranged hinge-like in the lower part 45 of the housing. The arm 49 has a short leg 49a (FIG. 4), which engages in a notch 50 of the upper housing part 31 in a latching fashion, as shown in dot-dash lines.

In contrast to the embodiment of FIG. 1, the embodiment of FIG. 2 provides at least one additional admission channel 51 in addition to the admission channel 35. This additional channel 51, for example, is connected in a known way to an outlet of the spit basin arrangement or to the outlet of a water jet pump of a dental apparatus and discharges into the distributor space 52 into which the liquid coming from the pump housing is also conducted. As in the exemplary embodiment of FIG. 1, the pipe-shaped nozzle 53 extends down into the proximity of the base of the collecting vessel 41 and is connected to the distributor space 52.

Since the pump is integrated into the upper housing part and since only one drive motor for the pump and the centrifuge is required, an extremely compact and economical separator device can be obtained. Of course, the measures for measuring the filling rate of the collecting vessel that were already set forth with reference to the embodiment of FIG. 1 can be advantageously incorporated into the embodiment of the device 101.

Another embodiment of the collector vessel of FIGS. 1 and 2 is illustrated in FIGS. 5-10. In this embodiment, the collector vessel, instead of being constructed as a one-piece container, is constructed of two parts, a cup-shaped outer container part 55, which opens towards the top and comprises essentially a cylindrical inside container wall and an insert part 56, which is introducable therein in a locking fashion. As in the exemplary embodiment of FIG. 2, the container part 55 contains an injected molded hub 57 that, as shown in FIG. 3, is rotationally fixed to the drive shaft of the motor, but which can be easily axially uncoupled therefrom in a detached fashion. The hub 57 has a bore 58 into which a shaft butt (not shown) can be introduced. This shaft butt, as shown in FIG. 2, engages into a corresponding fashioned spherical bearing 43 of FIG. 2.

An outer surface of a base or floor of the container 55 includes a plurality of ridges or blades 59 which proceed star-like from the axis of symmetry and generate an over-pressure in a space situated between the base of the container and housing during rotation of the container. This over-pressure prevents liquid from penetrating into the space or, respectively, forces liquid that may potentially be situated therein in an upward direction and into the outlet. The arrangement of the blades 59 can be best illustrated in FIG. 10, which is a bottom view of the container 55.

An insert part 56 is shown in FIGS. 6 and 9 and is composed of a plurality of partitions 56, which are arranged at uniform spacing from one another and are connected to one another by three elongated webs 61 which are arranged on the circumference of the partitions and extend up to a cover 63 which forms an upper edge. The partitions 60 are designed in the fashion of circular rings, each having the same outside diameter, but having differing inside diameters. As illustrated, they continually decrease in diameter as viewed from the bottom towards the top. This provides a result that in the assembled condition openings 62, which are formed between the hub, such as 57 and the inner edges or peripheries of the rings 60 are largest in the proximity of the base of the container and become increasingly smaller as the distance from the base increases. The opening 64 in the cover 63 is the smallest opening and, as illustrated, is substantially smaller than the next nearest opening 62a in the partition 60a. This noticeably smaller opening 64 ultimately defines the degree of separation of the particles to be separated and defines this upon rotation due to the circumferential speed prevailing at this location. The continuously decreasing inside diameter of the partition 60 from the base of the container up to the upper edge or cover of the container advantageously lies at an angular deviation $\alpha$, which is about 5° from the vertical, as illustrated. As illustrated in FIG. 6, the partitions 60 have outward peripheral gaps, such as 70, which will be closed when the insert part 56 is inserted into the container 55.

As already mentioned, the insert part 56 is introduced into the container 55 in a latching fashion, to which end are shown in detail in FIGS. 7 and 8. The container 55 contains an annular constriction or groove 67 in the region of its upper edge into which a likewise annular projection or rib 68 of the cover 63 of the insert part 56 engages when the insert part is placed into the container part 55 to provide a form-fit in the sense of a clamping connection.

Even though the overall collecting vessel in this embodiment, as in the embodiment of FIGS. 1 and 2, is provided as a one-use container, the two-part execution nonetheless has the advantage that the insert part 56, which becomes loaded with the centrifuge or separated particles, contains considerably less vessel material (plastic) than in the one-piece embodiments so that the emptying and preparation of the containers is less problematical than given the one-piece embodiments.

An extremely high separating efficiency can be achieved with the separator device set forth here. This potentially lies at 98%, dependent on the size of the particles. The separating efficiency of above 90% given a volume stream of about 700 ml/min. a liquid throughput is still achieved given a separating of solid particles having a grain size of 100 μm. The collecting vessel can accept several hundred grams of amalgam, dependent on the plurality and dimension of the individual chambers. The container is replaced when the container is filled and is supplied to a collecting institution for further disposal or processing which may include recovering of the solid materials.

Although it is expedient and advantageous to provide the container arrangement under the motor, an inverted arrangement is also conceivable. Thus, the motor may be arranged at the bottom and the container vessel may be arranged thereabove.

Although various minor modifications may be suggested by those versed in the art, it should be understood that we wish to embody within the scope of the patent granted hereon all such modifications as reasonably and properly come within the scope of our contribution to the art.

We claim:

1. In a device for use with a dental apparatus for separating solids from a liquid with centrifugal forces, said device including a housing, a centrifuge having a rotating container with a peripheral centrifugal wall being disposed in the housing and driven by a motor, said housing having an admission channel and an outlet channel so that liquid enriched with solids can be introduced through the admission channel into the housing and the rotating container with the solids being forced against the peripheral centrifugal wall as a consequence of centrifugal force and the liquid being pressed out of the container by overflow and being conducted into the outlet channel, the improvement comprising a collecting vessel being a component part of the rotating container of the centrifuge and having a container wall forming the centrifugal wall, said collecting vessel having a closed bottom and having a plurality of partitions extending transversely to an axis of the vessel to from a plurality of axially spaced chambers along the centrifugal wall of the vessel, said chambers being connected both to one another, as well as to the outlet channel by an opening in the center of each of the partitions so that a fluid flows from a chamber around an opening in the partitions to the next chamber and eventually out of the vessel as the particles are collected in each of the chambers, and said device having coupling means for detachably connecting the collecting vessel to a drive shaft of the motor with a torsionally rigid and axially detachable connection.

2. In a device according to claim 1, wherein the vessel has an axially extending hub and each of the openings in the partitions are concentric relative to the hub, said hub being part of said coupling means.

3. In a device according to claim 2, wherein the assembled condition, the hub of the collecting vessel lies against a stop on the drive shaft and is axially held with a fixed means, said shaft having a free end that extends through the hub and the vessel and is received in a bearing that is arranged adjacent the closed bottom of the vessel in a housing part that surrounds the collecting vessel.

4. In a device according to claim 3, wherein the housing part surrounding the collecting vessel forms a lower part of the device, said lower part having a cup shape with a closed base and surrounds a lower portion of said vessel, said housing having an upper part containing the admission channel, the outlet channel and a distributor space, said upper part supporting said drive motor.

5. In a device according to claim 4, wherein a pipe-shaped nozzle extends concentrically around the drive shaft into the collecting vessel and terminates adjacent the closed bottom of the collecting vessel for distributing the fluid into the vessel, said openings in the partitions being selected of such a size that a backup-free passage of liquid between the pipe forming the nozzle and the partitions is established.

6. In a device according to claim 1, which includes means for determining the degree of filling of the collecting vessel and for providing a signal when a given quantity of solids is reached.

7. In a device according to claim 6, wherein said means for determining the degree of filling includes means for sensing the start-up time for the drive motor.

8. In a device according to claim 7, wherein the means for sensing the start-up time of the drive motor includes a light barrier arrangement having a portion connected to the motor shaft and a portion connected to a stationary housing part adjacent the motor shaft.

9. In a device according to claim 1, wherein the housing includes a pump housing, said motor being connected to a rotary pump disposed in the pump housing for applying a pressure to the liquid entering the device.

10. In a device according to claim 9, wherein an upper part of the housing containing the pump housing has the admission channel in communication with the interior of the pump housing, said pump housing having a discharge with a check valve, said discharge of the pump being in communication with a distributor space of the housing, at least one additional admission channel for liquid being in communication with the distributor space downstream of said check valve, said distributor space having a tubular nozzle concentrically surrounding the drive shaft and extending into the collecting vessel to discharge fluid adjacent to the closed bottom of the collecting vessel.

11. In a device according to claim 1, wherein the collecting vessel is composed of two parts with an outer cup-shaped member receiving an insert having the partitions.

12. In a device according to claim 11, wherein the insert has a cylindrical outer surface consisting of a plurality of partitions axially spaced at a uniform spacing from one another extending up to an upper edge for the vessel, each of said partitions having an inside edge forming an opening with the openings having a different size.

13. In a device according to claim 12, wherein the openings in the partitions become continuously smaller as the distance from the base of the vessel towards the upper end of the vessel increases.

14. In a device according to claim 12, wherein the insert contains a cover forming an upper edge of the vessel, said cover having a discharge opening that is smaller than the openings in the partitions and being substantially smaller than the opening in the partition immediately adjacent thereto.

15. In a device according to claim 1, wherein an outside surface of the closed bottom of the vessel has a plurality of blades arranged star-like relative to the axis, said blades generating a pressure in a space between the housing and the closed bottom of the vessel during rotation of the vessel.

* * * * *